United States Patent [19]

Maeda et al.

[11] Patent Number: 5,747,495
[45] Date of Patent: May 5, 1998

[54] METHOD FOR TREATING HYPERTENSION USING PYRAZOLOPYRIMIDINE DERIVATIVES

[75] Inventors: Hiroshi Maeda, 3-21-19, Hotakubo, Kumamoto-shi, Kumamoto 862; Takaaki Akaike, Kumamoto; Yoichi Miyamoto, Ibaraki; Masaki Yoshida, Kumamoto, all of Japan

[73] Assignee: Hiroshi Maeda, Kumamoto, Japan

[21] Appl. No.: 700,848

[22] Filed: Aug. 21, 1996

[30] Foreign Application Priority Data

Aug. 22, 1995 [JP] Japan ................................ 7-213292

[51] Int. Cl.[6] ...................................... A61K 31/505
[52] U.S. Cl. ............................... 514/258; 544/262
[58] Field of Search ........................ 544/262; 514/258, 514/256

[56] References Cited

U.S. PATENT DOCUMENTS 3,474,098  10/1969  Hitchings ........................... 544/262

FOREIGN PATENT DOCUMENTS 94-13677  6/1994  European Pat. Off. .............. 544/262

*Primary Examiner*—Mark L. Berch
*Attorney, Agent, or Firm*—Wenderoth, Lind & Ponack

[57] ABSTRACT

Antihypertensive agents containing as its active ingredient the 4-amino-6-hydroxypyrazolo [3,4-d]pyrimidine(AHPP) or its derivatives represented by the general formula (I) below.

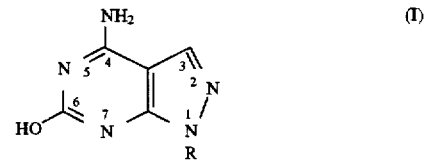

where

R is hydrogen atom, alkyl group or aryl group.

AHPP can be chemically synthesized by a reaction of 3-amino-4-cyanopyrazole and urea.

The antihypertensive agents of the present invention show a mild and reliable blood pressure lowering activity, and have a different mode of action from currently available antihypertensive agents.

10 Claims, No Drawings

METHOD FOR TREATING HYPERTENSION USING PYRAZOLOPYRIMIDINE DERIVATIVES

BACKGROUND OF THE INVENTION (a) Field of the Invention

The present invention relates to antihypertensive agents based on a new mode of action. More specifically, it relates to antihypertensive agents containing as its active ingredient pyrazolopyrimidine derivatives (b) Description of the Prior Art Hypertension is generally considered a risk factor of cardiac and circulatory diseases when either the diastolic blood pressure is higher than 90 mmHg or systolic blood pressure is higher than 140 mmHg. Medical intervention with antihypertension drugs is often introduced when the modified daily life style does not work or fails to lower the blood pressure or when diagnosed as a serious hypertension. Control of the blood pressure by treatment with therapeutic agent is extremely important to reduce the possible complication of hypertension in the heart, the brain and the kidney. Antihypertensive agents utilized for this purpose are classified mainly to the following four groups based on their difference of action in lowering blood pressure (uretics, sympathetic neuronal inhibitors, vasodilators such as calcium antagonists and angiotensin converting enzyme inhibitors (called ACE inhibitors).

Application of antihypertensive drugs with a moderate and reliable activity is generally recommended for the treatment of hypertensive patients in clinical practice. In addition special care should be taken in order to avoid rapid decline of blood pressure causing maladies in the patient's daily activity. Therefore, moderately effective antihypertensive agents which are capable of decreasing the blood pressure slowly, are in great demand.

Furthermore, in cases when the efficacy of a given antihypertensive agent is insufficient by increasing to some extent the dose of administration further increase of dosage of said agent is not usually advantageous and thus not recommended. However, a combination of such an agent with other types of antihypertensive drugs with a different mode of action is, therefore, preferred over simply escalating the dosage of a single agent of a single agent. Because better efficacy and fewer side effects are usually expected in the combination therapy. Therefore, development of antihypertensive agents with a novel mechanism of action will provide a better therapeutic alternative for such a clinical setting.

Accordingly, the present invention is directed to provide antihypertensive agents with a different mode of action from currently available antihypertensive agents, namely,by use of xanthin oxidase inhibitors. The results show a mild and reliable blood pressure lowering activity.

It is reported that endothelium derived relaxing factor (EDRF), an endogenous blood pressure lowering substance which dilates vascular wall by activating guanylate cyclase is present in the smooth muscle cells of the blood vessel (Pharma. Rev., 43, 109-142, 1991). It is also reported that the endothelium derived relaxing factor is now identified as nitric oxide (NO), and thus NO is inactivated extremely rapidly by the reaction with superoxide radicals generated in situ (Nature, 320, 454-456, 1986; PNAS, 93, 2248-2253, 1996; J. Biol. Chem., 266, 4244-4250, 1991).

Among a class of compound which is analogus to purine bases,like pyrazolopyrimidine derivatives, allopurinol is currently the agent of choice and commonly used for the treatment of gout and hyper uricemia. Another pyrazolopyrimidine derivative, 4-amino-6-hydroxypyrazolo [3,4-d] pyrimidine (AHPP) is reported to be a potent inhibitor of three major purine metabolic enzymes, xanthine oxidase (J. Biol. Chem., 226, 993–1000, 1957), xanthine dehydrogenase (Yokohama Med. Bull., 29, 53–58, 1978) and tryptophan pyrolase (Life Sci., 8, 843–851, 1969).

SUMMARY OF THE INVENTION

The inventors of the present invention have perceived the inhibitory effect of AHPP against xanthine oxidase, and discovered a novel activity of AHPP to reduce blood pressure by enhancing EDRF due to a decrease in superoxide or radical generation, more specifically by a novel mode between action by inhibiting the interaction of EDRF (which is now identified as nitric oxide) and superoxide ($O_2^-$). The latter consumes NO by a rapid reaction. Medication containing AHPP can suppress at xanthine oxidase, which, as a result, leaves NO unreacted and at high levels to dilate blood vessels AHPP will function as an effective component for the treatment of hypertension and lower blood pressure with a novel action mechanism, and will provide an opportunity to develop an alternative therapeutic choice of agents for the treatment of hypertension.

The present invention comprises antihypertensive agents containing as its active ingredient pyrazolopyrimidine derivatives represented by the general formula (I) below.

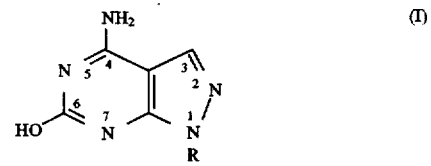

where R is hydrogen atom alkyl group, alkoxyl group or aryl group.

DESCRIPTION OF THE PREFERRED EMBODIMENT

Although a preferred compound of the active ingredient in the present invention is 4-amino-6-hydroxypyrazolo [3,4-d] pyrimidine(AHPP), which is a pyrazolopyrimidine derivatives wherein R indicated in the formula (I) is hydrogen atom, hydrogen can be replaced with alkyl groups alkoxyl group or aryl group. Alkyl or alkoxyl group replacing the hydrogen atom can be a straight or branched alkyl or alkoxyl group.

Illustrative examples of the derivatives used herein consists of $N_1$ proton replaced with methyl-, ethyl, n-propyl, isopropyl, n-butyl and isobutyl, methoxy-, ethoxy or phenyl groups.

AHPP can be chemically synthesized a reaction of 3-amino-4-cyanopyrazole and urea (J. Am. Chem. Soc., 78, 784–790, 1956).

Antihypertensive compounds according to the present invention can be administered either orally or parenterally in a form of a pure compound or composite containing the compounds of an appropriate dose, which is effective but without toxicity.

For oral administration of AHPP, the effective antihypertensive amount is 100–9000 mg/day./adult patient and can be taken once or more times of fractions dividedly, though the quantity of the compound will vary depending on the age, body weight and severity of the hypertension to be treated. For parenteral administration, intravenous injection is recommended but drip infusion may be performed.

For oral administration the compounds can be formulated into solid or liquid preparation such as capsules, pills, tablets, powders, solutions, suspensions, liposomes, emulsions etc. by use of the standard procedures. The solid unit dosage forms are those which are generally employed such as capsules or tablets. For parenteral administration the compound can be formulated as injectable dosages of solution or suspension of the compound in a physiologically acceptable diluent as a pharmaceutical carrier vehicle under the condition utilized for the standard procedure of parenteral preparation. It may be used as aqueous solution of 0.001–5.0% (w/w) for infusion.

Injectable formulation may also be prepared as separate units of tightly sealed vials or ampoules, one of them containing the compound (AHPP) in powder, and the other vial or ampoule contain diluents for dissolving the compounds (AHPP), which dissolve upon usage.

The antihypertensive agents according to the present invention not only show a mild and reliable blood pressure lowering activity, but also have a different mode of action from the currently available antihypertensive drugs. Therefore,improvement of efficacy and reduction of side effect are expected by administrating them combined with other types of antihypertensive agents with different mode of action

EXAMPLES

The present invention will now be described in detail with reference to the following examples which do not limit the scope of the invention.

[Procedure of Synthesis]

Example 1

Preparation of 3-amino-4-cyanopyrazole 2.5 g (20.5 mmole) of ethoxymethylene-malononitril was slowly added, to 3.4 g (57.8 mmole of 85% hydrazinehydrate solution. The same amount (2.5 g) of ethoxymethylene malononitril was further added. After cooling with cold water, and heating to 90°–100° C. for 1 hour, and the reaction mixture yielded a solid reaction product. The reaction mixture was added with 3.3 ml of water and allowed to stand at 4° C. for 12 hours. The resulting yellow-brown solid reaction product (3.0 g in dry weight) was filtered and washed with 1.5 ml of water and recrystallized from 6.0 ml of water, which yielded 2.5 g of 3-amino-4-cyanopyrazole.

Example 2

4-amino-6-hydroxypyrazolo(3, 4-d)pyrimidine 1.08 g of 3-amino-4-cyanopyrazole was mixed with 2.16 g of urea and heated at 200° C. for 20 minutes. The resulting solid substance was dissolved in 33 ml of 2N NaOH and mixed with active charcoal powder and heated at 90°–100° C. for 10 minutes. The solution was then filtered and the filtrate was added with 6 ml of anhydrous acetic acid yielding 1.3 g of crystalline after filtration. 0.6 g of the crystal of 4-amino-6-pyrazolo(3,4-d)pyrimidine (AHPP) was obtained by washing the crystalline with a mixed solution of formamide/dimethylformamide (2/1, v/v), formamide and acetone, successively. Physicochemical properties of thus obtained AHPP UV absorption; UV (λmax); at pH 11.0; 270 nm, at pH 1.0; 250 nm, Melting point; 320° C. Elementary analysis: theoretical values; C: 39.80, H: 3.30, N: 46.40 experimental results; C: 38.60, H: 3.27, N: 44.75 FAB-MS (Neg): [M-H]-: 150.00 (Fast atom bombard mass spectrometry) [Formulations]

Example 3

Preparation of Tablets of AHPP

AHPP, lactose and starch were mixed and a moistured granules are prepared by addition of polyvinylpyrrolidon solution and magnesium stearate. A preparation of 500 mg/tablet was obtained by pressure tablet extruder with magnesium stearate, followed by drying. A representative weight ratios of the component of the tablet ingredients are;

| AHPP | 100 |
|---|---|
| lactose | 235 |
| starch | 50 |
| 10% polyvinylpyroridon solution | 50 |
| magnesium stearate | 5 |

Example 4

Preparation of Suspension Syrup of AHPP 1.5 g of sorbitol and 0.005 g of glycerol were dissolved in 3.0 L of water, and the solution was added to a portion of a benzoic acid water solution prepared separately. A representative contents of the components used were as follows;

| AHPP | 25 g |
|---|---|
| sorbitol | 1.5 g |
| glycerol | 0.005 g |
| dispersion type carboxy methyl cellulose | 0.005 g |
| water | filled up to 5 L. |

Example 5

Inhibitory Effect of AHPP Against Uric Acid Production by Xanthine Oxidase In Vitro Rate of uric acid production was determined by measuring the increase of an optical absorbance at 290 nm in 50 mM phosphate buffer solution (pH 7.5) containing 2.19–21.9 µmole/L of xanthine and 0–0.44 µmole/L AHPP in the presence of cow milk xanthine oxidase in the final concentration of 3.33 mU/ml. The results showed that uric acid production by xanthine oxidase was inhibited by AHPP in a dose-dependent manner. The inhibitory coefficient (Ki) of AHPP for xanthine oxidase was determined to be 0.2 µM, by an analysis of its reaction velocity kinetics. The inhibitory action of AHPP was also demonstrated as a competitive inhibition.

[Experiments of Biochemical and Biological Effects]

Example 6

Inhibitory Effect of AHPP against Superoxide Production by Xanthine Oxidase In Vitro Production of superoxide radicals was determined by measuring a chemiluminescence observed in 100 mM phosphate buffer (pH 7.4) containing 10 µmole/L lucigenin and 10 a mole/L xanthine in the presence of 20 U/ml of xanthine oxidase derived from cow milk. Further, the inhibition of superoxide generation by the AHPP was evaluated by addition of 0–100 µmole/L of AHPP into the reaction mixture. AHPP was shown to inhibit superoxide production by xanthine oxidase in a dose-dependent manner. The results are shown in the Table 1.

TABLE 1

Effect of AHPP to inhibit superoxide generation by xanthine oxidase with hypoxanthine

| Concentration of AHPP (μmole/L) | Integral value of intensity of chemiluminescence/10 min[a] |
|---|---|
| 0 | $5.2 \times 10^6$ count |
| 1 | $4.4 \times 10^6$ count |
| 10 | $1.6 \times 10^6$ count |
| 100 | $8.0 \times 10^4$ count |

[a]Average of two measurements

Example 7

Synergistic Vascular Relaxation Effect to Acetylcholine of Rabbit Aortic Ring by AHPP Aortic ring with a diameter of 5 mm was prepared from chest aorta of New Zealand White female rabbits with a body weight of 2.5–3.0 kg. The rings were surgically prepared and hanged into the organ bath containing 20 ml of Krebs solution, which was kept at 37° C. and supplemented with 95% $O_2$ and 5% $CO_2$, for determination of the tension.

Aortic ring relaxation by 0–1mole/L acetylcholine was measured in the prescence of 0, 100, and 300 μmole/L of AHPP, after aortic ring contraction was induced by 0.15 μmole/L phenylepherine. As shown in Table 2 the dose of phenylepherine required for 50% relaxation of phenylepherine-induced aortic ring contraction was reduced depending on the concentration of AHPP present in the solution.

TABLE 2

Effect of AHPP on the inhibition of vascular relaxation by acetylcholine

| Concentration of AHPP (μmole/L) | Amount of acethylcholine required to inhibit 50% relaxation of aorta ring[a] |
|---|---|
| 0 | 0.11 |
| 100 | 0.075 |
| 300 | 0.055 |

[a]Average of four measurements

Example 8

Effect of Intravenous Injection of AHPP on the Blood Pressure of Spontaneously Hypertensive Rats Eighteen weeks old spontaneously hypertensive 8 male rats weighing 300–400 g were intravenously infused with 50 mg/kg of AHPP in a solution dissolved in 1 ml of 0.1 M NaOH for 5 minutes (8 rats), and mean arterial blood pressure was measured under anesthesia. Eight control rats were received only 0.1 M NaOH by intravenous infusion.

Mean arterial blood pressure of the treated groups showed a gradual decrease up to 72% the values before the treatment, at 70 minutes after AHPP treatment. Whereas, no such drop of blood pressure was evident in the untreated control group. The results are shown in Table 3.

TABLE 3

Hypotensive effect of AHPP in spontaneous hypertensive rats (values are average of 8 rats ± SE)

| Time (min) after iv infection of AHPP | Mean arterial blood pressure: 100% = preinjection value | |
|---|---|---|
| | AHPP group | Control (vehicle only) |
| 0 | 100 | 100 |
| 5 | 98.3 ± 2.7 | 105.5 ± 7.5 |
| 10 | 92.2 ± 6.1 | 107.3 ± 6.9 |
| 15 | 91.1 ± 5.6 | 106.1 ± 6.3 |
| 20 | 86.9 ± 8.0 | 105.0 ± 6.6 |
| 30 | 81.7 ± 5.0 | 103.3 ± 4.2 |
| 40 | 77.7 ± 5.2 | 100.5 ± 3.1 |
| 50 | 76.1 ± 7.2 | 98.9 ± 3.3 |
| 60 | 73.5 ± 7.5 | 97.5 ± 4.1 |
| 70 | 72.4 ± 6.6 | 96.7 ± 5.0 |

Dose of AHPP. 50 mg/kg in rats. 0.33 mmol/ml, 1.0 ml/5 min. See text for details. Average value of 8 measurements ±SD.

Example 9

Effects of Oral Administration of AHpp on the Blood Pressure of Spontaneously Hypertensive Rats Four male spontaneously hypertensive rats with a body weight of 300–4000 g and 4 male rats with a body weight of 200–300 g were orally given with 100 mg/kg of AHPP and a systolic blood pressure in tail artery was examined 4 hours after the treatment. Systolic blood pressure of the treated group was reduced to 70% the value of before

We claim:

1. A method for treating hypertension, which comprises administering to a patient in need thereof a therapeutically effective amount of a compound according to the Formula (I):

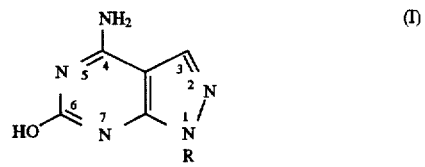

where R is hydrogen atom, alkyl group, alkoxyl group or aryl group.

2. A method for treating hypertension, which comprises administering to a patient in need thereof a therapeutically effective amount of a composition comprising:
a compound according to the Formula (I):

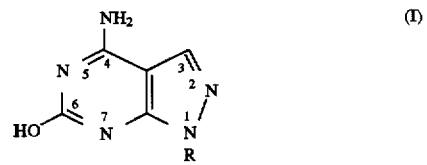

where R is hydrogen atom, alkyl group, alkoxyl group or aryl group, and a pharmaceutically acceptable carrier.

3. The method according to claim 2, wherein R is aryl group.

4. The method according to claim 1, wherein R is hydrogen atom.

5. The method according to claim 1, wherein R is alkyl group.

6. The method according to claim 1, wherein R is alkoxyl group.

7. The method according to claim 1, wherein R is aryl group.

8. The method according to claim 2, wherein R is alkoxyl group.

9. The method according to claim 2, wherein R is hydrogen atom.

10. The method according to claim 2, wherein R is alkyl group.

* * * * *